United States Patent
Hourticolon et al.

(10) Patent No.: US 6,683,224 B1
(45) Date of Patent: Jan. 27, 2004

(54) PROCESS FOR THE PRODUCTION OF FATTY ALCOHOLS

(75) Inventors: Roland Hourticolon, Leichlingen (DE); Guenther Demmering, Solingen (DE); Hans-Peter Kubersky, Solingen (DE); Lothar Friesenhagen, Duesseldorf (DE); Friedrich Hommers, Duesseldorf (DE); Juergen Latzel, Wuppertal (DE); Eberhard Peukert, Hilden (DE); Hans-Guenther Richard, Duesseldorf (DE); Udo Kreutzer, Monheim (DE)

(73) Assignee: Cognis Deutschland GmbH & Co. KG, Dusseldorf (DE)

( * ) Notice: Subject to any disclaimer, the term of this patent is extended or adjusted under 35 U.S.C. 154(b) by 0 days.

(21) Appl. No.: 10/304,445

(22) Filed: Nov. 26, 2002

Related U.S. Application Data

(63) Continuation of application No. 09/924,327, filed on Aug. 8, 2001, now abandoned, which is a continuation of application No. 09/550,734, filed on Apr. 17, 2000, now abandoned, which is a continuation of application No. 08/433,780, filed on May 3, 1995, now abandoned.

(51) Int. Cl.[7] ............................................. C07C 29/136

(52) U.S. Cl. ........................ 568/864; 568/854; 554/141; 554/143

(58) Field of Search ................................ 584/141, 143; 568/856, 864

(56) References Cited

U.S. PATENT DOCUMENTS 5,324,871 A * 6/1994 Carduck et al. ............. 568/884

* cited by examiner

*Primary Examiner*—Deborah Carr
(74) *Attorney, Agent, or Firm*—John E. Drach

(57) ABSTRACT

Naturally occurring fats, oils and fatty derivatives are continuously hydrogenated to fatty alcohols in a fixed-bed reactor in the presence of hydrogen in excess and hydrogenation catalysts under static pressures of 50 to 300 bar and at temperatures of 160 to 320° C. The liquid product is cooled and the excess hydrogen is returned to the reactor entrance by a gas circulation pump as a recycle gas after separation of the liquid product. The expense involved in cooling and reheating the recycle gas is eliminated without any reduction in the quality of the fatty alcohol produced providing the recycle gas is returned to the reactor entrance without reheating and the hydrogenation reaction is carried out under static pressures of at least 200 bar.

39 Claims, 1 Drawing Sheet

PROCESS FOR THE PRODUCTION OF FATTY ALCOHOLS

"This application is a continuation of application Ser. No. 09/924,327, filed Aug. 8, 2001 abandoned, which is a continuation of Ser. No. 09/550,734, filed Apr. 17, 2000, now abandoned, which in turn is a continuation of Ser. No. 08/433,780, filed May 3, 1995, now abandoned."

BACKGROUND OF THE INVENTION

1. Field of the Invention

This invention relates to an improved process for the continuous production of fatty alcohols by the continuous hydrogenation of naturally occurring fats, oils and fatty derivatives. More specifically, the present invention relates to a process for the continuous hydrogenation of fatty acid esters to saturated or unsaturated fatty alcohols in a fixed-bed reactor in the presence of at least stoichiometric amount of hydrogen wherein unreacted hydrogen is recycled without reheating by means of a recirculation pump after separation from the liquid product.

2. Description of the Related Art

In the known process, the starting material, for example fatty acid methyl ester, is delivered by high-pressure pumps into the installation where it is mixed with compressed hydrogen, heated with the compressed hydrogen to the reaction temperature and introduced into the reactor from above. In addition to the ester group, carbon double bonds are also hydrogenated on the copper-containing catalyst so that, even where unsaturated esters are used, only saturated fatty alcohols are formed. In cases where a copper-free catalyst, on which the ester bond is selectively hydrogenated, is used, unsaturated fatty alcohols are formed from unsaturated fatty acid esters or glycerides.

After passing through the reactors, the reaction mixture is cooled and separated in a separator into the liquid phase and the gas phase. The liquid phase is vented and delivered to the methanol separation stage while the gas phase, which consists mainly of hydrogen, is circulated via a compressor.

In the methanol separation stage consisting of an evaporator, the fatty alcohol is freed from the methanol and may then be used without further purification.

The invention also encompasses the direct catalytic hydrogenation of glyceride oils to fatty alcohol and propane-1,2-diol and of fatty acids to fatty alcohol, as described for example in U.S. Pat. Nos. 4,982,020; 4,855,273; and 4,935,556, the entire contents of each of which is incorporated herein by reference.

The known processes are characterized by a high excess of hydrogen, typically of the order of 100 to 200 moles of hydrogen per mole of ester. The large volume of gas which is circulated involves considerable outlay on equipment, more particularly for cooling and reheating, which is normally carried out in several stages. After leaving the reactor, the gas/liquid mixture passes through the heat exchanger used to preheat the starting material. This is followed by cooling with water. After separation of the liquid phase, the recycle gas is delivered together with fresh hydrogen into the feed line for fatty acid methyl ester by a gas circulation pump, is mixed with fatty acid methyl ester and the resulting mixture is preheated in the heat exchanger mentioned. Finally, the mixture passes through a peak heater.

The problem addressed by the present invention was to reduce the outlay on equipment for cooling and reheating the unreacted recycle gas involved in the process mentioned at the beginning without any reduction in the quality of the fatty alcohol produced.

The solution to this problem is realized by returning the unreacted recycle gas the reactor entrance without reheating and carrying out the hydrogenation reaction at a pressure of at least 200 bar and, more particularly, at least 250 bar.

SUMMARY OF THE INVENTION

Other than in the claims and in the operating examples, or where otherwise indicated, all numbers expressing quantities of ingredients or reaction conditions used herein are to be understood as modified in all instances by the term "about".

A process for the continuous production of a saturated or unsaturated fatty alcohol by hydrogenation of a fatty acid, a naturally occurring fat, or a fatty acid derivative been discovered. The process comprises contacting a fatty acid or fatty acid derivative with at least a stoichiometric amount of hydrogen at a pressure of from about 50 to about 300 bar and at a temperature of from about 160 to about 320° C. in the presence of a catalyst to form a liquid product phase comprised of at least a fatty alcohol having the same number of carbon atoms as the fatty acid, a naturally occurring fat, or a fatty acid derivative and unreacted hydrogen. The unreacted hydrogen is then separated from the liquid product phase and is recycled to the beginning of the process without reheating. Because the hydrogen is recycled without further heating, the process economics are considerably improved without sacrificing the quality of the fatty alcohol produced by the process.

DESCRIPTION OF THE PREFERRED EMBODIMENTS

Figure 1:
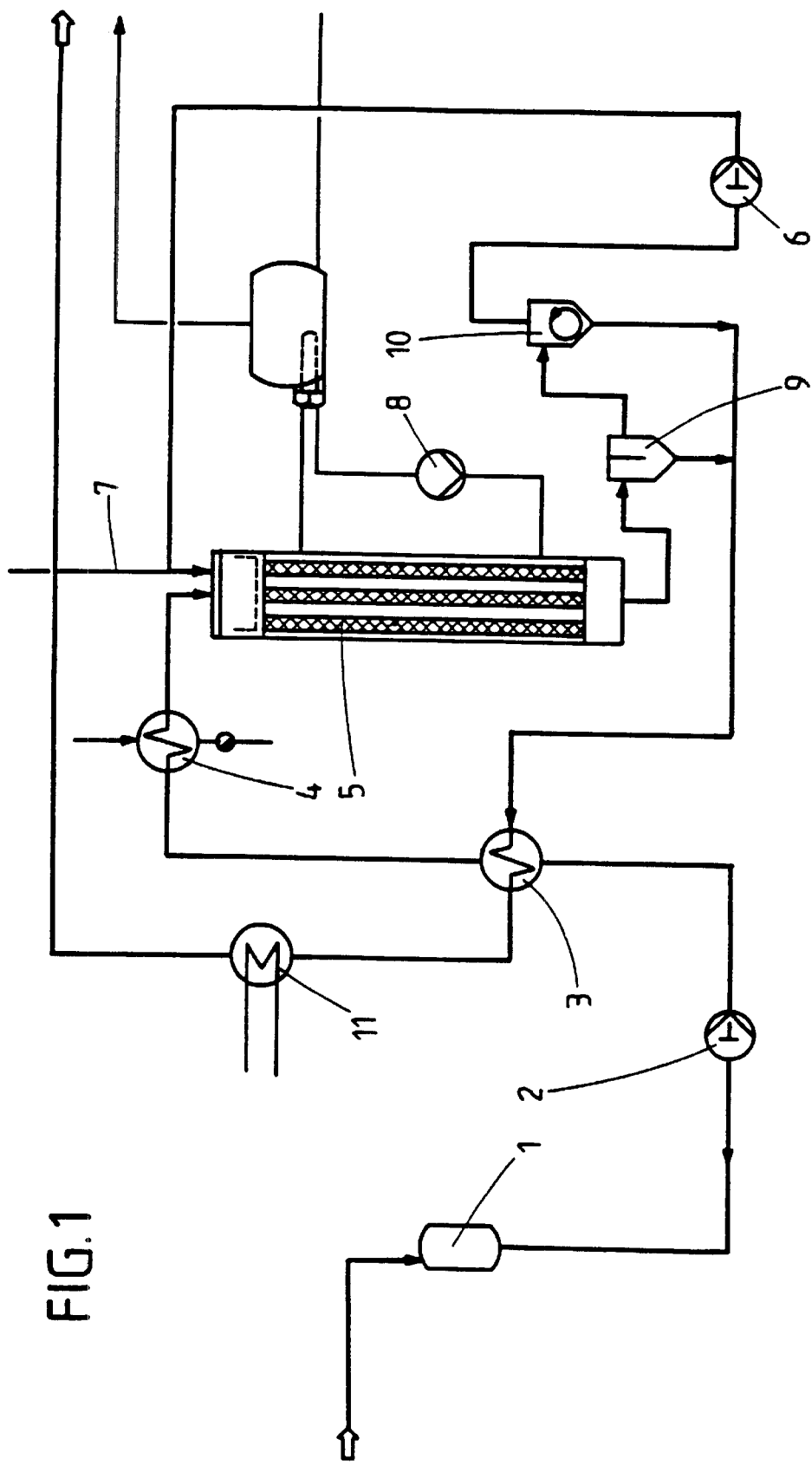
FIG. 1 is a schematic representation of a commercial process for the hydrogenation of fatty acid methyl ester to fatty alcohols.

According to the invention, the unreacted hydrogen from the process for making fatty alcohols by hydrogenation of a fatty acid, a naturally occurring fat, or a fatty acid derivative is recycled into the front of the process without reheating. Surprisingly, high yields can still be achieved providing the hydrogenation reaction is carried out under static pressures of at least 200 bar and preferably under static pressures of at least 270 bar. Not only the outlay on equipment, but also energy consumption is reduced.

Since the hydrogenation reaction is exothermic, the heated reaction is dissipated either by cooling the reactor internally or externally by cooling the recycle gas. The heat dissipated may advantageously be used for preheating or peak heating of the starting product.

According to one preferred embodiment, the hydrogenation process is carried out in a cooled tube-bundle or tube reactor. A tube-bundle reactor is a reactor comprised of a plurality of small diameter tubes arranged inside a large diameter tube wherein the long axes of the small tubes and the large tube are parallel. Each individual small diameter tube is packed with catalyst. The recycle gas is preferably returned to the reactor without cooling. The heat of reaction is dissipated solely by cooling the reactor.

However, the process according to the invention may also be carried out in a tower reactor. A tower reactor is a single cyclindrical reactor in which the catalyst is packed and the hydrogenation process is carried out over the catalyst by contacting the fatty acid, a naturally occurring fat, or a fatty acid derivative with hydrogen in a cocurrent or a countercurrent manner in either type of reactor. In the case wherein the hydrogenation reaction is carried out in an uncooled tower reactor and, after leaving the reactor, the recycle gas is cooled to dissipate the heat of reaction before or after removal of the liquid product. In contrast to the prior art, however, the issuing recycle gas is not cooled any more than is necessary to dissipate the heat of reaction.

Since, according to the invention, the recycle gas is only cooled slightly, if at all, the heat to be dissipated can no longer be used to preheat the liquid starting product, as in the prior art. In order, nevertheless, to minimize energy consumption, the liquid product is cooled in a heat exchanger which preheats the liquid feed, more particularly after separation of the gas phase.

In the process according to the invention, the hot hydrogen gas under high pressure is circulated by a gas circulation pump. The exposure to high temperatures means that the pump has to be correspondingly designed. This can be achieved in a simple and economical manner by circulating the recycle gas with a piston pump of which the cylinder and piston are connected to the valves by pendulum lines of which the volume is at least three times the swept volume of the pump. There is no continuous flow of gas in these pendulum lines, merely a back and forth swinging movement. Accordingly, the hot working valves of the pump can be arranged at a sufficient distance from the cylinder and piston with their sensitive packings and drive elements. Although it delivers a hot gas, the pump—except for the valves—can be kept at a relatively low temperature. A circulation process such as this for hot gases, more particularly under high pressures, is known from DE-AS 1 044 343 and from DE-PSS 1 048 665 and 1 077 367. Reference is specifically made at this juncture to the disclosures of these documents.

In the process according to the invention when the starting fatty acid derivative is a fatty acid methyl ester, the recycle gas contains a relatively high percentage of methanol compared to known processes wherein the recycle gas is cooled and then reheated. According to the invention, the resulting displacement in the equilibrium reaction to the left can be eliminated by maintaining minimum pressures so that sufficiently high yields are still obtained.

It has surprisingly been found that the reaction temperature can be distinctly lower in the process according to the invention than in the known processes mentioned above without any reduction in the conversion expressed by the residual saponification value. Thus, the hydrogenation reaction for the production of saturated fatty alcohols is preferably carried out at reaction temperatures of 190 to 220° C. The lesser tendency towards the formation of secondary products and the lower temperatures to which the catalyst is exposed are both advantages. The preferred catalyst is a copper-zinc catalyst.

Reaction temperatures of 290 to 320° C. are preferred for the production of unsaturated fatty alcohols.

Besides the high methanol content, the consistently high temperature of the recycle gas also leads to a relatively high water content which cannot be removed from the circuit by virtue of the absence or substantial absence of cooling. The water of reaction formed during the hydrogenation of the fatty acid components of the starting product requires a special choice of catalyst. Accordingly, it is proposed that, where the starting product contains more than 10% by weight of fatty acid (or where the starting product has an acid value above 25), the hydrogenation reaction should be carried out with a catalyst which cannot be deactivated by steam.

The process according to the invention is particularly suitable for the hydrogenation of $C_{8-18}$ fatty acid methyl esters.

Test results obtained with an industrial hydrogenation plant of the type shown in FIG. 1 are explained in the following.

FIG. 1 schematically illustrates the construction of a plant for the hydrogenation of fatty acid methyl ester to fatty alcohols. Fatty acid methyl ester is introduced into the plant by a high-pressure pump 2 via an intermediate tank 1. The liquid starting material is preheated by a heat exchanger 3, brought to the reaction temperature by a steam-operated peak heater 4 and introduced from above into a tube-bundle reactor 5. The recycle gas is also delivered to the head of the reactor 5 together with fresh hydrogen (pipe 7) by a gas circulation pump 6. A pump 8 passes a heat transfer oil through the reactor 5 for cooling.

The product leaving the reactor 5, a gas/liquid mixture, is separated up in separators 9,10 and, after cooling in the heat exchanger 3 and a following cooler 11 operated with cooling water, the liquid phase is delivered to the methanol separation stage. The gas phase is returned to the reactor 5 as recycle gas by the gas circulation pump 6.

The following examples are meant to illustrate but not to limit the invention.

EXAMPLE 1

Table 1 shows the results of making saturated fatty alcohols from coconut oil methyl ester using a copper-containing catalyst by two different processes. The first line shows typical results obtained by the known process mentioned above in which the recycle gas is cooled to a relatively low temperature and is reheated to the reaction temperature behind the gas circulation pump. The last line shows the saponification as a measure of the yield. It can be seen that, with sufficiently high reaction pressures, the saponification values obtained by the known process can again be achieved. Compared with the prior art, however, the process according to the invention involves considerably less outlay on equipment.

The results in the last two lines reflect a surprisingly high conversion although the reaction temperature was distinctly reduced.

TABLE 1

|  | LHSV ($h^{-1}$) | $H_2$ ($m^3/h$) | Reaction temperature (° C.) | Reaction pressure (bar) | Saponification value (SV) |
|---|---|---|---|---|---|
| Prior Art | 1.48 | 30 | 215 | 250 | 1.0–1.1 |
| Invention | 1.0 | 40 | 219 | 250 |  |
|  | 1.45 |  |  |  |  |
|  | 1.48 | 20 | 223 | 270 | 1.1 |
|  | 1.48 | 20 | 215 | 270 | 1.1 |
|  | 1.48 | 20 | 215 | 230 | 1.65 |
|  | 1.48 | 30 | 221 | 250 | 1.3 |
|  | 1.48 | 30 | 221 | 270 | 1.05 |
|  | 1.48 | 20 | 198 | 270 | 1.0 |
|  | 1.25 | 20 | 210 | 270 | 0.85 |

EXAMPLE 2

These tests were also carried out in the plant described above. The starting product was palm kernel oil methyl ester.

A copper-containing catalyst was used for the production of saturated fatty alcohols.

Table 2 shows the results obtained. For substantially the same residual saponification value, the percentage of secondary products is reduced to a very considerable extent by comparison with the known process.

TABLE 2

|  | LHSV ($h^{-1}$) | $H_2$ ($m^3/h$) | Reaction temperature (° C.) | Reaction pressure (bar) | Saponification value | Percentage of secondary products (%) |
| --- | --- | --- | --- | --- | --- | --- |
| Prior Art | 1.56 | 30 | 215 | 250 | 1.0 | 0.67 |
| Invention | 1.56 | 20 | 215 | 270 | 1.15 | 0.4 |
|  | 1.56 | 20 | 200–205 | 270 | 1.1 | <0.1 |

The test only has to be terminated after about 60 days through deactivation of the catalyst.

The catalyst depreciation amounted to 0.001 kg of catalyst per kg of fatty alcohol and was therefore distinctly lower than in known processes.

LIST OF REFERENCE NUMERALS IN FIG. 1

1 Intermediate tank
2 High-pressure pump
3 Heat exchanger
4 Peak heater
5 Reactor
6 Gas circulation pump
7 Pipe for fresh hydrogen
8 Pump
9 Separator
10 Separator
11 Cooler

What is claimed is:

1. A process for the continuous production of a saturated or unsaturated fatty alcohol comprising the steps of: (1) contacting liquid feed which is a fatty acid or fatty acid derivative with at least a stoichiometric amount of hydrogen at a pressure of from about 50 to about 300 bar and at a temperature of from about 160 to about 320° C. in the presence of a catalyst to form a liquid product phase and unreacted hydrogen; (2) separating said liquid product phase from said unreacted hydrogen; (3) cooling the liquid product phase in a heat exchanger which also preheats the liquid feed; and (4) without reheating, recycling said unreacted hydrogen to step (1).

2. The process of claim 1 wherein the amount of hydrogen in step (1) is from about 10 to about 500 times the stoichiometric amount.

3. The process of claim 1 wherein said pressure is at least about 200 bar.

4. The process of claim 3 wherein said pressure is at least about 250 bar.

5. The process of claim 1 wherein said temperature is from about 190 to about 220° C.

6. The process of claim 1 wherein said temperature is from about 290 to about 320° C.

7. The process of claim 1 wherein said catalyst is comprised of copper.

8. The process of claim 1 wherein a fatty acid derivative is employed which is a $C_{8-16}$ fatty acid methyl ester.

9. The process of claim 1 wherein step (1) is carried out in a cooled tube-bundle reactor.

10. The process of claim 1 wherein step (1) is carried out in a tower reactor.

11. The process of claim 1 wherein step (1) is carried out in a cooled tube reactor.

12. The process of claim 1 wherein step (4) is carried out by cooling the unreacted hydrogen before recycling it to step (1).

13. The process of claim 1 wherein step (4) is carried out with a gas piston pump containing valves and a cylinder and a piston connected to the valves by pendulum lines, wherein the volume of the pendulum lines is at least three times the swept volume of the pump.

14. The process of claim 8 wherein step (1) is carried out in a cooled-tube bundle reactor.

15. The process of claim 8 wherein step (4) is carried out by cooling the unreacted hydrogen before recycling it to step (1).

16. A process for the continuous production of a saturated or unsaturated fatty alcohol comprising the steps of: (1) contacting liquid feed which is a fatty acid or fatty acid derivative with at least a stoichiometric amount of hydrogen at a pressure of from about 50 to about 300 bar and at a temperature of from about 160 to about 320° C. in the presence of a catalyst to form a liquid product phase and unreacted hydrogen; (2) separating said liquid product phase from said unreacted hydrogen; and (3) without reheating, recycling said unreacted hydrogen to step (1).

17. A process for the continuous production of a saturated or unsaturated fatty alcohol comprising the steps of: (1) contacting liquid feed which is a fatty acid or fatty acid derivative with at least a stoichiometric amount of hydrogen at an elevated pressure and at an elevated temperature in the presence of a catalyst to form a liquid product phase and unreacted hydrogen; (2) separating said liquid product phase from said unreacted hydrogen; (3) cooling the liquid product phase in a heat exchanger which also preheats the liquid feed; and (4) without reheating, recycling said unreacted hydrogen to step (1).

18. A process for the continuous production of a saturated or unsaturated fatty alcohol comprising the steps of: (1) contacting liquid feed which comprises a fatty acid or fatty acid derivative with at least a stoichiometric amount of hydrogen in the presence of a catalyst to form a liquid product phase and unreacted hydrogen; (2) separating said liquid product phase from said unreacted hydrogen; and (3) without reheating, recycling said unreacted hydrogen to step (1).

19. A process for the continuous production of a saturated or unsaturated fatty alcohol comprising the steps of: (1) contacting the liquid feed which upon hydrogenation gives a saturated or unsaturated fatty alcohol with hydrogen to form a liquid product phase and unreacted hydrogen; (2) separating the liquid product from the unreacted hydrogen; and (3) without reheating, recycling the unreacted hydrogen to step (1).

20. The process of claim 19 wherein in step (1) a hydrogenation catalyst is employed.

21. The process of claim 20 wherein said catalyst is comprised of copper.

22. The process of claim 19 wherein step (1) is carried out in a cooled tube-bundle reactor.

23. The process of claim 19 wherein step (1) is carried out in a tower reactor.

24. The process of claim 19 wherein step (3) is carried out by cooling the unreacted hydrogen before recycling it to step (1).

25. The process of claim 19 wherein step (3) is carried out with a gas piston pump containing valves and a cylinder and a piston connected to the valves by pendulum lines, wherein the volume of the pendulum lines is at least three times the swept volume of the pump.

26. The process of claim 19 wherein the liquid feed is a fatty acid, a naturally occurring fat, a fatty acid derivative, or a mixture of two or more thereof.

27. In a process for the continuous production of a saturated or unsaturated fatty alcohol, by contacting a liquid feed with hydrogen, the improvement wherein unreacted hydrogen is recycled without reheating.

28. The process of claim 27 wherein the liquid feed is a fatty acid and/or a fatty acid derivative.

29. The process of claim 27 wherein from about 10 to about 500 times the stoichiometric amount of hydrogen is used in the process.

30. The process of claim 27 wherein the process is carried out in the presence of a catalyst.

31. The process of claim 27 wherein the process is carried out at an elevated temperature and pressure.

32. In a process for the continuous production of a saturated or unsaturated fatty alcohol product by contacting a liquid feed with hydrogen, the improvement wherein the alcohol product is cooled in a heat exchanger that preheats the liquid feed.

33. The process of claim 32 wherein the liquid feed is a fatty acid and/or a fatty acid derivative.

34. The process of claim 32 wherein from about 10 to about 500 times the stoichiometric amount of hydrogen is used in the process.

35. The process of claim 32 wherein the process is carried out in the presence of a catalyst.

36. The process of claim 32 wherein the process is carried out at an elevated temperature and pressure.

37. In a process for the continuous production of a saturated or unsaturated fatty alcohol product by contacting a liquid feed with hydrogen, the improvement wherein the process is carried out in a single reactor.

38. The process of claim 37 wherein the reactor is a cooled tube reactor.

39. The process of claim 37 wherein the reactor is a tower reactor.

* * * * *